United States Patent [19]

Johans

[11] Patent Number: 4,644,960
[45] Date of Patent: Feb. 24, 1987

[54] DEVICE FOR MAKING ELECTRICAL CONNECTION TO AN ELECTROLYTE, AND SYSTEM EMPLOYING SAME

[75] Inventor: Thomas G. Johans, Des Peres, Mo.

[73] Assignee: Arrow International, Inc., Reading, Pa.

[21] Appl. No.: 779,394

[22] Filed: Sep. 23, 1985

[51] Int. Cl.[4] ............................................. A61M 5/00
[52] U.S. Cl. ..................................... 128/786; 604/20; 604/66
[58] Field of Search ............... 128/783, 784, 786, 715, 128/642, D13; 604/20, 21, 50, 66, 86, 64

[56] References Cited

U.S. PATENT DOCUMENTS

| 3,085,577 | 4/1963 | Berman et al. | 128/641 |
| 3,553,583 | 1/1971 | Wiley | 604/253 |
| 3,604,411 | 9/1971 | Schuler | 128/639 |
| 3,731,679 | 5/1973 | Wihelmson et al. | 128/D13 |
| 3,863,504 | 2/1975 | Borsanyi | 128/D13 |
| 4,244,364 | 1/1981 | Grushkin | 128/D13 |
| 4,484,135 | 11/1984 | Ishihara et al. | 604/66 |
| 4,564,016 | 1/1986 | Maurice et al. | 604/20 |

Primary Examiner—Edward M. Coven
Attorney, Agent, or Firm—Albert L. Free

[57] ABSTRACT

An adapter suitable for ready insertion into a fluid line extending between a source of electrically-conductive fluid and a part of a living body, to enable convenient electrical contact to the fluid. The adapter is T-shaped and has a through-bored portion on the opposite ends of which quick-disconnect luer-lock connectors are formed to receive the ends of the adjacent tubing sections. An electrical connector pin extends through the stem of the T, at right angles to the through bore, to contact the fluid in the through bore; the external end of the pin is provided with a quick-disconnect connector terminal so that it can easily be connected to and disconnected from associated electrical equipment, such as an ECG monitor. The body of the adapter may be of molded plastic, and the entire unit so inexpensive that it can economically be discarded after use. In addition to ECG monitoring the adapter is specially suitable for use in regional block anesthesia.

1 Claim, 8 Drawing Figures

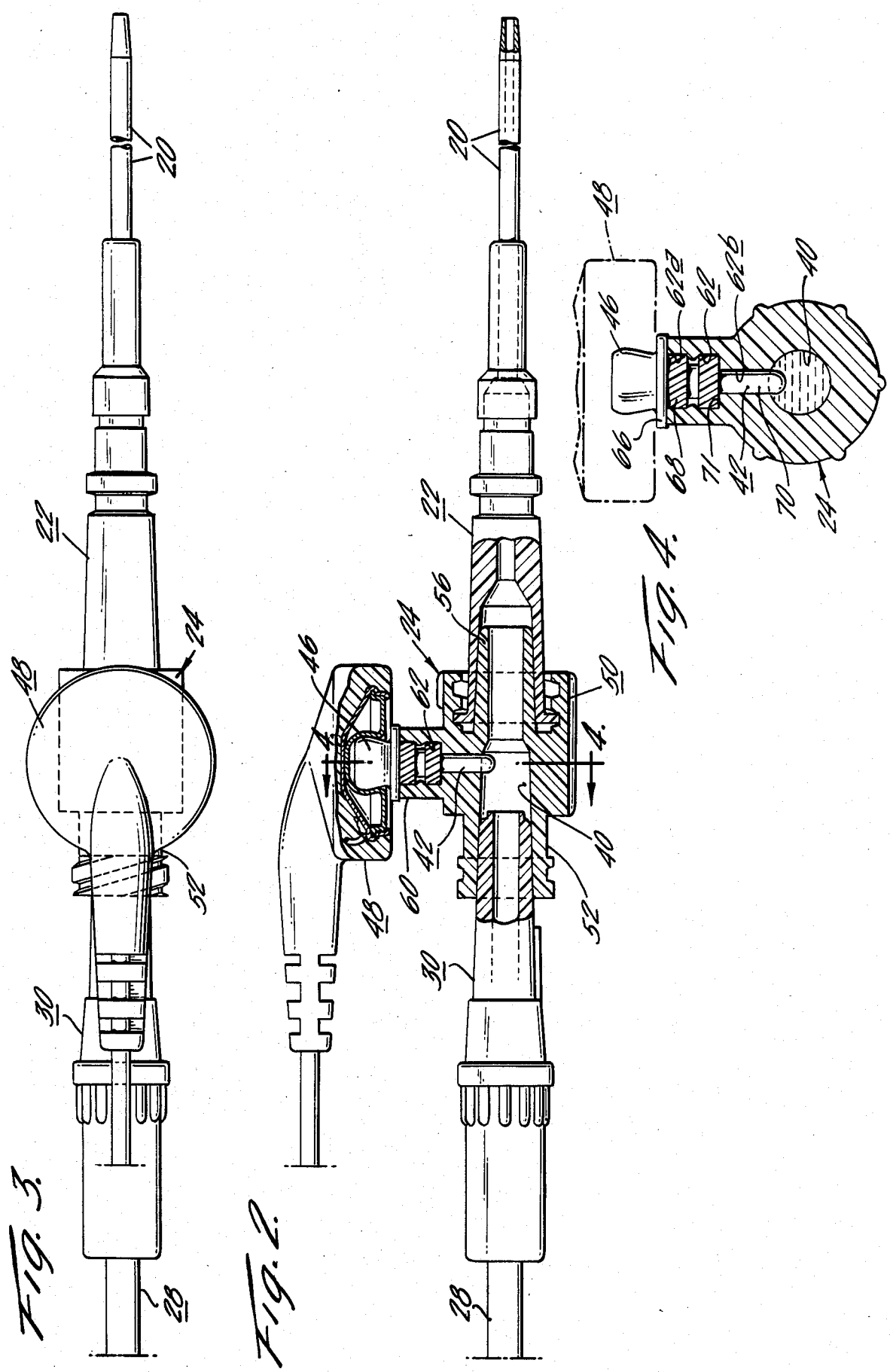

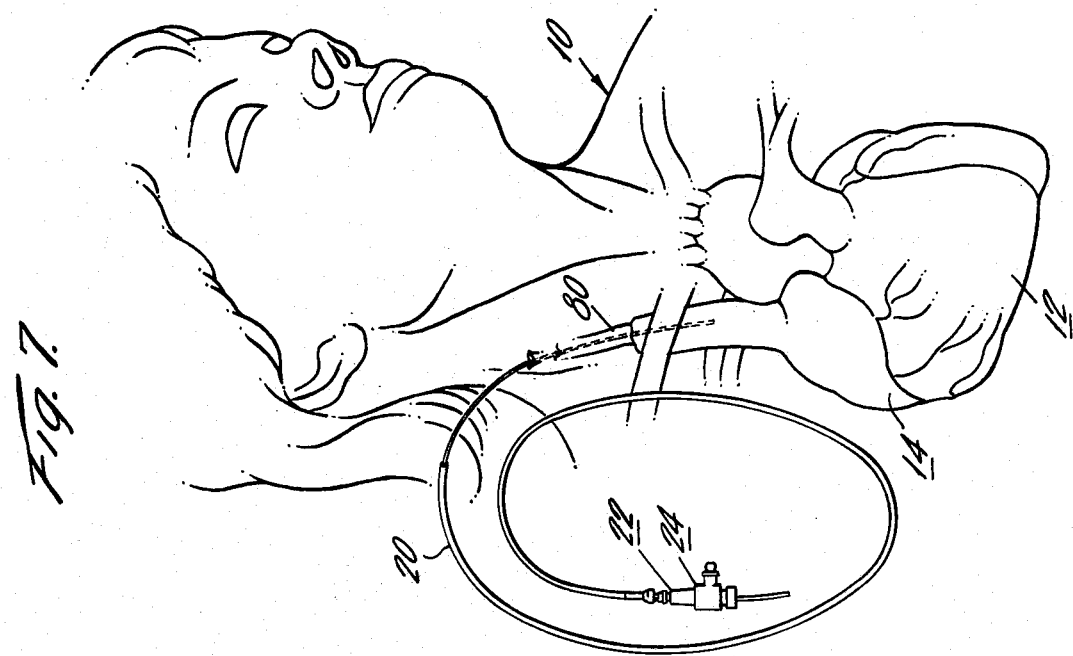
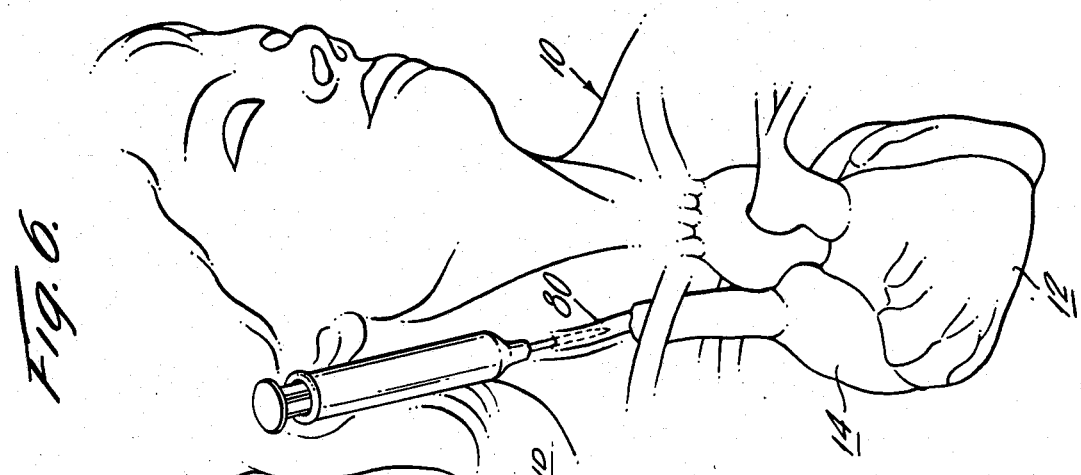
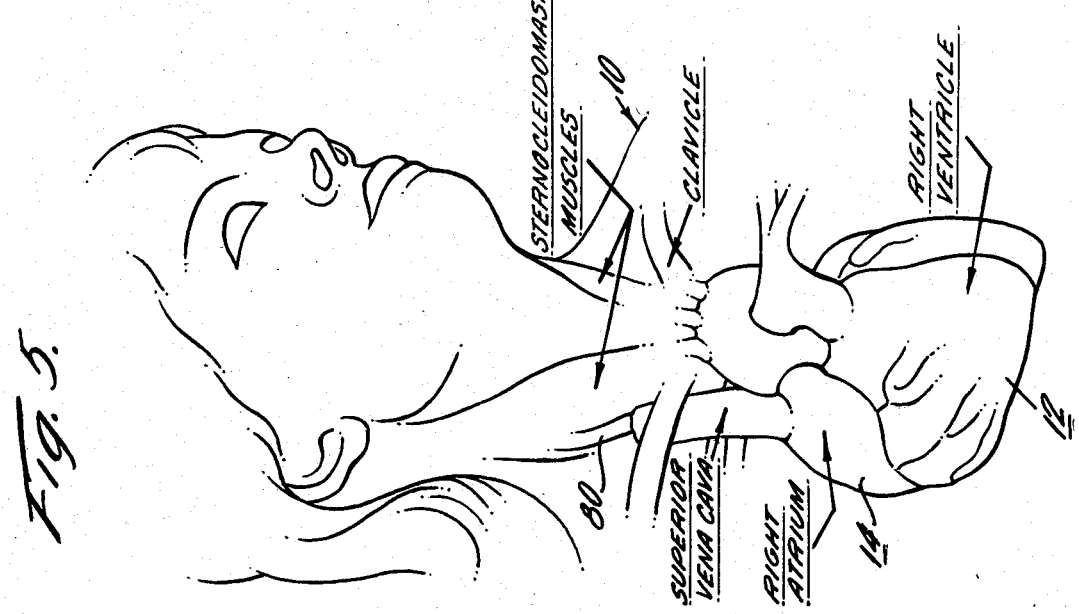

DEVICE FOR MAKING ELECTRICAL CONNECTION TO AN ELECTROLYTE, AND SYSTEM EMPLOYING SAME

BACKGROUND OF THE INVENTION

The invention relates generally to a device and system for making electrical connection to an electrolyte, and especially to such device and system in which electrical connection is provided to an electrolyte contained within a length of tubing extending into a human body, as is the case in a catheter electrode, for example.

There are a variety of applications in which it is desired to provide an electrical connection to an electrolyte within a catheter inserted into the human body, and it is with respect to such applications that the present invention will be described in detail.

A specific use of such an arrangement is in right atrial electrocardiography (RAECG). In this technique a catheter containing an electrolyte in the form of an ionic salt is inserted into the right atrium of a human heart to serve as a right atrial electrode. That is, the electrically-conductive electrolyte serves as a long electrode extending from the atrium to a portion of the catheter external to the body where an electrical connection is made to the electrolyte to derive the desired measurements with respect to electrical activity within the atrium. Such RAECG is a known technique for facilitating central venous catheter placement, for more accurately diagnosing atrial dysrhythmias, and for recognizing posterior myocardial ischemia/infarction.

In order to make the necessary electrical connection to the electrolyte at a point external to the body, it has previously been the custom to employ an all-metal stopcock in line between the catheter tubing and the source of the electrolyte; a sterilized alligator clip was secured to the all-metal stopcock, and a conductive lead attached to the alligator clip constituted the ECG lead by which the electrical variations to be studied were carried from the alligator clip to the ECG monitor.

A similar arrangement has been used in connection with the administration of regional block anesthetic in liquid form, where the liquid anesthetic, such as lidicane, is electrically conductive and is delivered from a syringe through a catheter-over-needle device to the site of the nerve to be anesthetized. By applying a low voltage to the electrolyte, the nerve is caused to twitch when the needle has been inserted to the desired point where the liquid anesthetic reaches the nerve site, the nerve twitch providing an indication to the anesthetist that he has reached the desired site. For this purpose also it is known to use an all-metal stopcock as the electrode to which the external voltage is applied.

Such an all-metal stopcock and alligator clip arrangement is relatively expensive, as a result of which it cannot economically be discarded after use and hence must be resterilized on each occasion of its reuse; also, since its exterior is of metal it is exposed to anomalous environmental electrical currents due to chance grounding or leakage currents, which may interfere with the desired ECG display and possibly do injury to the patient.

Accordingly, it is an object of the invention to provide a new and useful device and system for providing electrical connection to an electrolyte.

Another object is to provide such device and system which is especially adapted for making electrical connection to an electrolyte used as a liquid electrode extending through a catheter into the human body.

A further object is to provide such device and system which is very inexpensive to make and hence can economically be discarded after each use, thus avoiding the need for sterilization upon each reuse.

It is also an object to provide such apparatus in which the electrical connection is completely insulated from the environment during use.

A still further object is to provide such a device which is quick and easy to insert into the electrolyte system.

SUMMARY OF THE INVENTION

These and other objects of the invention are realized by the provision of an adapter suitable for insertion in-line between a pair of electrolyte-containing lengths of tubing to permit flow of electrolyte through it from one length of tubing to the other, while also providing an electrical connection to the electrolyte in the adapter, and which comprises a body of non-metallic material having a bore extending through it for passing the electrolyte, the body being shaped to provide quick-disconnect hydraulic connectors for permitting tubing to be connected to each end of the bore; an electrically conductive pin extends transversely through a wall of the body into the bore and is adapted to make electrical contact with the electrolyte in the bore, the external end of the pin being shaped to provide a quick-disconnect electrical connector. Preferably the quick-disconnect hydraulic connector at one end of the bore is a male Luer lock connector and that at the other end of the bore is a female Luer lock connector; the quick-disconnect electrical connection is preferably a male ECG-type connector nipple.

The body is preferably of molded plastic material and comprises a first generally cylindrical portion coaxial with the bore and a second generally cylindrical portion having its axis substantially normal to the axis of the bore to form a T configuration, the pin then extending along the axis of the second body portion from the exterior into the bore.

In a complete apparatus for providing an electrolyte electrode system, one Luer lock connector of the adapter may be connected to tubing leading to the source of electrolyte while the other may be connected to tubing in the form of a catheter which is designed to be placed into a human body, for example in the atrium of the heart. The female ECG-type electrical connector can be snapped into position over the exterior end of the electrically conductive pin in the adapter, and a lead therefrom connected to the associated electrical apparatus, in the preferred embodiment an ECG monitor. Particularly where the adapter is used in connection with the delivery of an electrically-conductive anesthetic, one Luer lock connector of the adapter may be connected directly to an electrolyte-filled syringe, and the other may be connected directly to a catheter-over-needle device or other rigid structure, rather than to flexible tubing.

With this arrangement, all that need be on hand at the outset are two lengths of standard catheter tubing with one appropriate Luer lock connector at one end of the catheter tubing and another at one end of the electrolyte supply tubing, a female electrical connector at the end of the lead connecting to the ECG monitor, and the adapter of the invention. To assemble the system, the Luer lock connectors of the adapter are connected to the corresponding Luer lock connectors on the two tubing ends, the ECG lead connector is snapped onto the ECG connector nipple of the adapter, and the system is ready for operation. When the procedure is completed, the tubings and leads can be removed from the adapter and the adapter thrown away. Preferably, the adapter is supplied initially in a sterile package with plastic or rubber protective caps on the Luer connections where the tubing will later be connected, and with another plastic cap covering the external electrical connection, thereby protecting all these elements from contamination and/or damage.

Not only is the adapter extremely inexpensive and easy to use, but it presents no electrically conductive exterior surfaces and hence is not susceptible to accidental contact with environmental electrical potentials which might interfere with the measurement procedures or possibly injure the patient.

BRIEF DESCRIPTION OF DRAWINGS

These and other objects and features of the invention will be more readily appreciated from a consideration of the following detailed description, taken with the accompanying drawing, in which:

FIG. 2 is a side elevational view, partly in section, showing a preferred embodiment of the adapter of the present invention;

FIG. 3 is a top view of the adapter of FIG. 2;

FIG. 4 is a vertical transverse sectional view taken on lines 4—4 of FIG. 2; and FIGS. 5-8 are perspective views showing successive steps in the installation and connection to a patient of an ECG catheter system using the adapter of the present invention.

DETAILED DESCRIPTION OF SPECIFIC EMBODIMENTS

Figure 1:
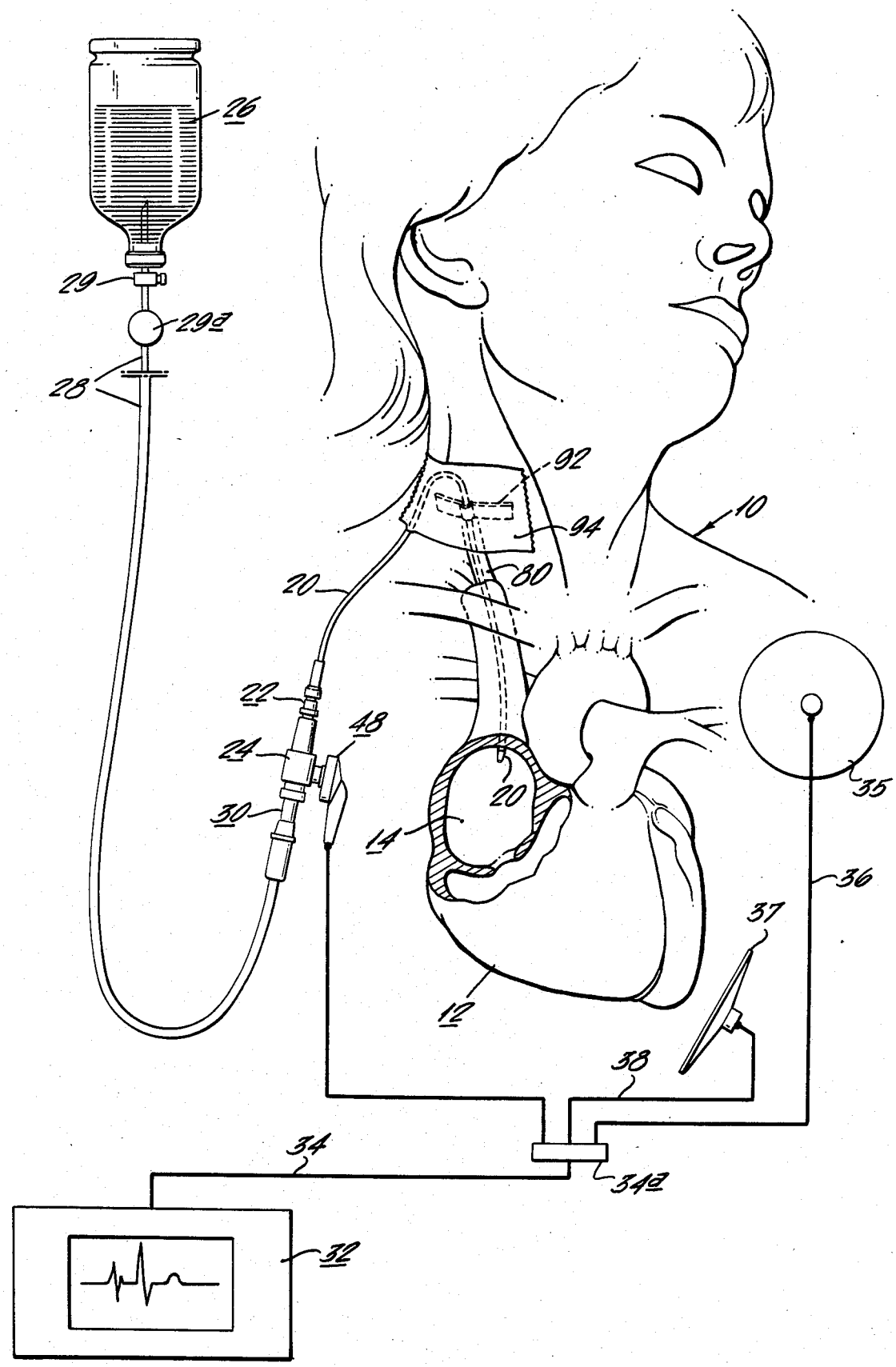
FIG. 1 is an elevational view showing an ECG system utilizing the adapter of the invention in a system for monitoring electrical conditions in a living human heart.

Referring first to FIG. 1, there are shown relevant portions of a human body 10 containing a heart 12 having an atrium 14 into which, in this example of use, one open end of catheter tubing 20 has been inserted through the right jugular vein by known techniques to be described hereinafter, for the purpose of right atrial electrocardiography. The other end of the catheter tubing 20 is provided with the female Luer connector 22, connected to a male Luer connection at one end of a T-shaped adapter 24.

A source of electrolyte 26 is connected to and communicates with one end of the electrolyte supply tubing 28 by way of conventional manually-operable control valves 29,29A, which are at least partially opened to permit slow electrolyte flow during the RAECG monitoring. Tubing 28 is provided at its other end with a male Luer lock connector 30, which is connected to a female Luer lock formed on the end of adapter 24 opposite from connector 22. Also shown schematically is an ECG monitor unit 32 and an electrically-conductive ECG lead 34 extending between the electrical connector of adapter 24 and the monitor, by way of a suitable plug connection 34A. Also provided is a conventional left-arm electrode 35 and attached lead 36, and a ground electrode lead 37 and corresponding ground electrode 38; the monitor, its leads and the placement of the electrodes may be entirely conventional.

Referring to FIGS. 2-4 for further details of the adapter 24, in the present embodiment of the invention it is inserted between the adjacent ends of the two lengths of electrolyte tubing 28 and 20, and provides electrolyte communication between them through a central axial bore 40 within the adapter. An electrically-conductive pin 42 extending through the wall of the adapter makes electrical contact at its inner end with the electrolyte in the bore, and is provided at its outer end with a suitable external electrical connector 46 in the form of a male snap-on nipple, to which the female snap-on ECG connector 48 is connected to complete the system. Accordingly, electrolyte from the electrolyte source 26 can flow through both lengths of tubings 28 and 20 and the adapter in series, to the remote end of the catheter tubing 20 in the heart, as desired, while the varying electrical potentials in the electrolyte are supplied to the ECG monitor by way of the ECG lead 34 and the electrolyte-contacting pin 42 of the adapter.

The adapter 24 comprises an integral molded body 50 of a suitable inert, sterilizable plastic material, the left-hand end of which as viewed in FIG. 2 is formed into the female Luer connector 52 for connection to the electrolyte source tubing 28 by way of the male Luer connector 30; the right-hand end of the adapter is formed to constitute a male Luer connector 56 for connection to the female Luer connector 22 on the catheter tubing 20. The adapter body 50 also comprises a generally cylindrical stem portion 60 which extends upwardly to form a T-shaped configuration and contains a bore 62 extending normally to the axis of bore 40. Bore 62 has a larger-diameter upper portion 62A and a smaller-diameter lower portion 62B.

The pin 42 comprises the male connector nipple 46, a circular flange 66 at the lower side of the nipple, a large-diameter shaft portion 68 just beneath the flange, and a smaller-diameter shaft portion 70 at its lower end. The flange 66 of the connector pin abuts the upper end of the body stem portion 60 when fully inserted as shown, the larger-diameter portion 68 of the pin being received in the seat 71 formed by the lower end of the larger-diameter bore portion 62A in the stem portion 60. The lower, smaller diameter, portion of the pin shaft extends through the smaller-diameter portion 62B of bore 62, with its tip extending somewhat into the bore 40 so as to contact the electrolyte. The smaller-diameter bore in the stem which receives the lower part of the pin is so sized, with respect to the pin, as to provide a close fit for the pin, which is seated and positioned by forcing it downwardly into the position shown. The head of the electrically conductive pin is formed as shown to constitute the nipple 46 suitable for receiving the female snap-on quick-disconnect connector 48 of the ECG lead.

The adapter is readily manufactured by conventional molding techniques, after which the small-diameter end of the pin 42 is coated with any suitable harmless adhesive, pressed into bore 62 until flange 66 abuts the top of stem 60, and left in position until the adhesive sets and hardens. The entire adapter is then preferably sterilized and sterilely packaged in a hermetically sealed plastic envelope; readily-removable protective plastic caps may be placed over the two hydraulic connectors and the electrical connector of the adapter prior to packaging thereof.

A typical RAECG procedure in which the adapter of the invention is useful is illustrated by FIGS. 5-8 and 1.

FIG. 5 shows the patient's upper body and heart, including the right atrium and superior vena cava, and the jugular vein 80 through which the catheter is to be introduced into the atrium.

FIG. 6 illustrates venipuncture of the jugular preparatory to introducing the usual catheter-guiding wire, which is then advanced into the atrium.

FIG. 7 shows the catheter tubing 20 placed over the wire and being advanced over the wire toward the atrium, with the male Luer lock connector of adapter 24 connected to the female Luer lock connector of the catheter tubing at the end remote from the patient.

Figure 8:
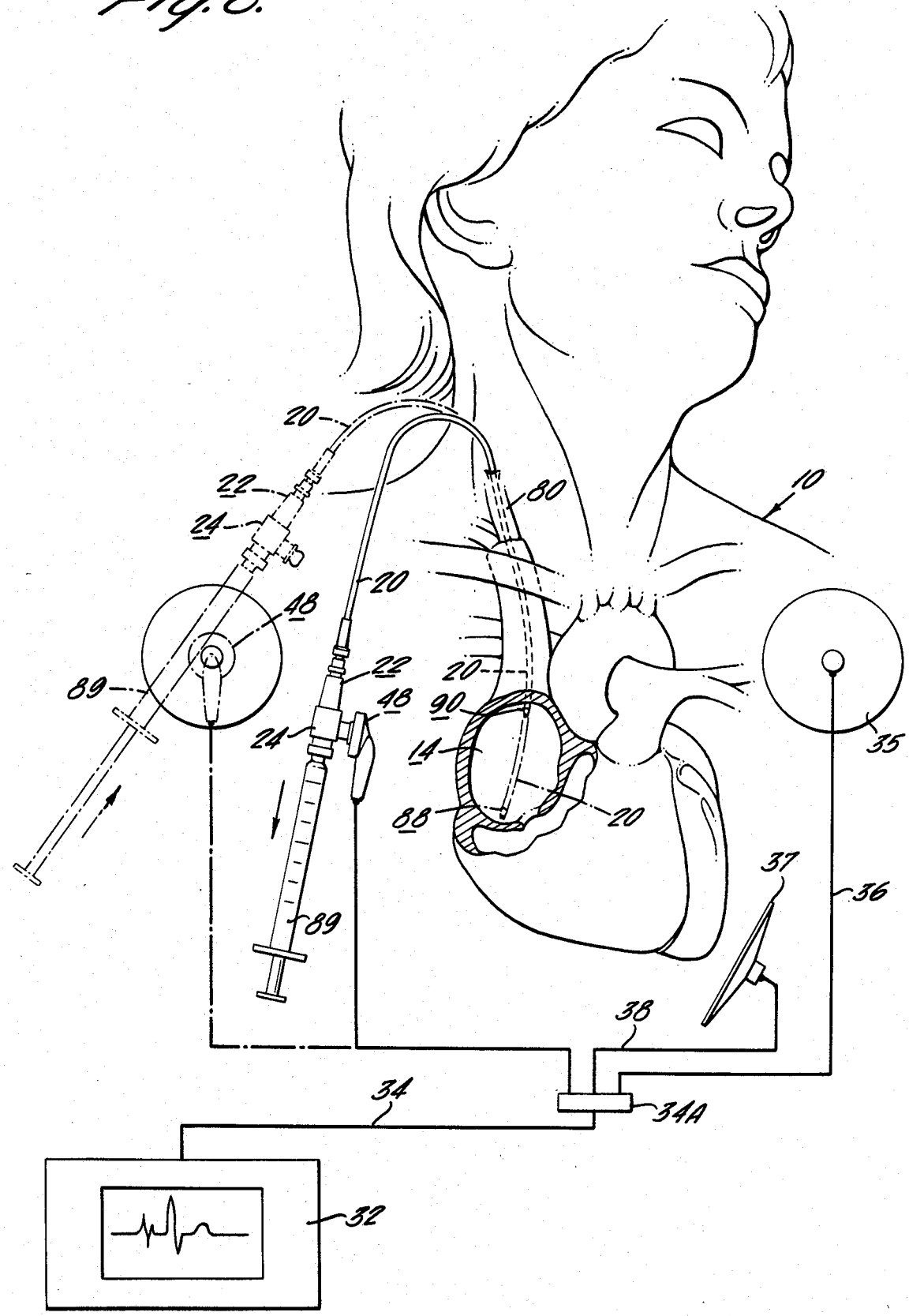

FIG. 8 shows in broken-line the next step wherein the catheter has been advanced far into the atrial cavity to position 88, the wire withdrawn, the ECG monitor system connected, and a syringe 89 filled with saline solution connected to the electrolyte-input end of the adapter to enable flushing-out of the adapter and catheter tubing, after which as shown in full-line the catheter is partially withdrawn until its forward tip is at the desired position 90, as can be determined with the aid of observations of the ECG trace during the withdrawal.

FIG. 1 shows the next step in which the catheter 20 has been immobilized by placing a clamping device 92 about it, suturing the clamping device to the skin of the neck, and covering the device with an adhesive site covering 94. As shown, the electrolyte supply tubing 28 has been connected to the adapter and the electrolyte supply valves turned on. The ECG traces thereafter observed provide the desired medical information regarding variations in electrical potential in the atrium.

The adapter described is inexpensive to make and, accordingly, can be discarded after each use. During use, it presents no external conductive surfaces, and hence is not subject to interference by contact with ambient sources of electrical potential. A very inexpensive, effective, and easy-to-use adapter has therefore been provided for insertion between a pair of electrolyte-containing tubings, to provide electrical connection to the electrolyte within the tubing, as desired.

As noted previously, the electrical connection may be used for purposes other than for ECG monitoring, for example as an electrode for applying a nerve-activating voltage during administration of a regional nerve block, and the tubing connected to each end of the adapter need not be flexible, but may instead be rigid as when a syringe is directly coupled to one end of the adapter and a catheter-over-needle device directly connected to the other end of the adapter.

Accordingly, while the invention has been described in detail with particular reference to specific embodiments thereof, it will be understood that it can be embodied in a variety of forms diverse from those specifically shown and described, without departing from the spirit and scope of the invention.

What is claimed is:

1. In a system for providing electrical connection between a chamber of the heart of a living person and external electrical medical equipment, comprising a catheter adapted to extend at one end through a blood vessel and into said heart chamber, a source of electrolyte, a tube connected at one end to said source for filling said catheter with a flow of electrolyte, a device for making electrical contact to said electrolyte, and an electrical lead connected between said device and said medical equipment, the improvement wherein said device comprises:

a T-shaped adapter made of electrically insulating material and having a cylindrical cross-bar portion and a cylindrical stem portion extending at right angles to said cross-bar portion at the center of the length thereof, said cross-bar portion having a first cylindrical bore extending axially through its length, said stem portion having a second cylindrical bore extending axially through it to intersect said first bore, and the two opposite ends of said cross-bar portion comprising quick-disconnect hydraulic connectors providing hydraulic communication between one end of said first bore and the other end of said catheter remote from said heart chamber, and between the other end of said first bore and the other end of said tube remote from said electrolyte source;

said adapter further comprising a metallic electrode one end of which extends through said second bore and into the interior of said first bore to contact said electrolyte at a predetermined position and the other end of which extends outwardly from the exterior of said stem portion and comprises a quick-disconnect snap-on electrical connector for enabling quick connection to, and quick disconnection from, said electrical connection of said electrical lead connected to said medical equipment, said electrical connector also comprising a circumferential outwardly-extending flange intermediate its opposite ends, said second bore having an internal shoulder against which said flange bears to hold said one end of said electrical connector in said predetermined position.

* * * * *